(12) United States Patent
Oppenheimer

(10) Patent No.: US 9,422,313 B2
(45) Date of Patent: *Aug. 23, 2016

(54) METHODS OF FORMING 4-CHLORO-2-FLUORO-3-SUBSTITUTED-PHENYLBORONIC ACID PINACOL ESTERS AND METHODS OF USING THE SAME

(71) Applicant: Dow AgroSciences LLC, Indianapolis, IN (US)

(72) Inventor: Jossian Oppenheimer, Midland, TX (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,096

(22) Filed: Nov. 6, 2014

(65) Prior Publication Data

US 2015/0203514 A1 Jul. 23, 2015

Related U.S. Application Data

(63) Continuation of application No. 13/722,471, filed on Dec. 20, 2012, now Pat. No. 8,912,339.

(60) Provisional application No. 61/582,173, filed on Dec. 30, 2011.

(51) Int. Cl.
*C07D 213/72* (2006.01)
*C07F 5/02* (2006.01)
*C07F 5/04* (2006.01)
*C07D 213/807* (2006.01)
*C07F 1/02* (2006.01)

(52) U.S. Cl.
CPC ............ *C07F 5/025* (2013.01); *C07D 213/807* (2013.01); *C07F 1/02* (2013.01); *C07F 5/04* (2013.01)

(58) Field of Classification Search
CPC .................................................. C07D 213/803
USPC .......................................... 546/310; 558/288
See application file for complete search history.

(56) References Cited

U.S. PATENT DOCUMENTS

| | | | |
|---|---|---|---|
| 7,314,849 B2* | 1/2008 | Balko et al. | 504/244 |
| 7,611,647 B2* | 11/2009 | Arndt et al. | 260/665 R |
| 7,915,200 B2 | 3/2011 | Epp et al. | |
| 7,964,758 B2 | 6/2011 | Matoba et al. | |
| 8,754,110 B2* | 6/2014 | Oppenheimer et al. | 514/352 |
| 8,822,730 B2* | 9/2014 | Oppenheimer | 568/1 |
| 2009/0182168 A1 | 7/2009 | Arndt et al. | |

FOREIGN PATENT DOCUMENTS

| | | |
|---|---|---|
| CN | 101970446 | 2/2011 |
| EP | 2181098 | 5/2010 |
| EP | 2332914 | 6/2011 |
| WO | 2009029735 | 3/2009 |

OTHER PUBLICATIONS

Cammidge et al. Journal of Organic Chemistry, 2003, 68(17), 6832-6835.*
Harwig et al. Tetrahedron Letters, 2008, 49(19), 3152-3156.*
Cammidge et al., Application of the Suzuki Reaction as the Key Step in the Synthesis of a Novel Atropisomeric Biphenyl Derivative for Use as a Liquid Crystal Doplant, , Journal of Organic Chemistry, May 15, 2003, pp. 6832-6835, vol. 68—No. 17, American Chemical Society.
Harwig et al., Synthesis and characterization of 2,6-difluoro-4-carboxypheylboronic acid and a biotin derivative thereof as captors of anionic aqueous [18F]-fluoride for the preparation of [18F/19F]-labeled aryltrifluoroborates with high kinetic stability, Science Direct, Tetrahedron Letters, Jan. 16, 2008, pp. 3152-3156, vol. 49—No. 19, Elsevier Ltd.
International Search Report and Written Opinion for International Application No. PCT/US2012/070967, dated Apr. 10, 2013.
Lennox et al, Selection of boron reagents for Suzuki-Miyaura coupling, Chem Soc Rev, Oct. 3, 2013, pp. 412-443, vol. 43, The Royal Society of Chemistry.

* cited by examiner

*Primary Examiner* — Nizal Chandrakumar
(74) *Attorney, Agent, or Firm* — Michael J. Terapane; Magleby Cataxinos & Greenwood

(57) ABSTRACT

Methods include formation of 4-chloro-2-fluoro-3-substituted-phenylboronic acid pinacol esters. The method comprises contacting a 1-chloro-3-fluoro-2-substituted benzene with an alkyl lithium to form a lithiated 1-chloro-3-fluoro-2-substituted benzene. The lithiated 1-chloro-3-fluoro-2-substituted benzene is contacted with an electrophilic boronic acid derivative to form a 4-chloro-2-fluoro-3-substituted-phenylboronate. The 4-chloro-2-fluoro-3-substituted-phenylboronate is reacted with an aqueous base to form a (4-chloro-2-fluoro-3-substituted-phenyl)trihydroxyborate. The (4-chloro-2-fluoro-3-substituted-phenyl)trihydroxyborate is reacted with an acid to form a 4 chloro-2-fluoro-3-substituted-phenylboronic acid. The 4-chloro-2-fluoro-3-substituted-phenylboronic acid is reacted with 2,3-dimethyl-2,3-butanediol to form 4-chloro-2-fluoro-3-substituted-phenylboronic acid pinacol esters . Methods of using 4-chloro-2-fluoro-3-substituted-phenylboronic acid pinacol esters to produce 6-(4-chloro-2-fluoro-3-substituted-phenyl)-4-aminopicolinates are also disclosed.

15 Claims, No Drawings

METHODS OF FORMING 4-CHLORO-2-FLUORO-3-SUBSTITUTED-PHENYLBORONIC ACID PINACOL ESTERS AND METHODS OF USING THE SAME

CROSS-REFERENCE TO RELATED APPLICATION

This application is a continuation of U.S. patent application Ser. No. 13/722,471, filed Dec. 20, 2012, pending, which application claims the benefit of U.S. Provisional Patent Application Ser. No. 61/582,173, filed Dec. 30, 2011, the disclosure of each of which is hereby incorporated herein in its entirety by this reference.

TECHNICAL FIELD

Embodiments of the present disclosure relate to methods of forming 4-chloro-2-fluoro-3-substituted-phenylboronic acid pinacol esters and to methods of using 4-chloro-2-fluoro-3-substituted-phenylboronic acid pinacol esters. Embodiments of the present disclosure also relate to methods of forming 2-(4-chloro-2-fluoro-3-methoxyphenyl)-4,4,5,5-tetramethyl-1,3,2-dioxaborolane (PBE-pinacol), and to methods of using the same.

BACKGROUND 4-chloro-2-fluoro-3-methoxyphenylboronic acid (PBA) and 2-(4-chloro-2-fluoro-3-methoxyphenyl)-1,3,2-dioxaborinane (PBE) are useful intermediates in the preparation of 6-(poly-substituted aryl)-4-aminopicolinate compounds and 2-(poly-substituted aryl)-6-amino-4-pyrimidinecarboxylic acid compounds, which are useful as herbicides. PBA may be esterified using 1,3-propanediol to form PBE.

For some operations it would be desirable to be able to efficiently crystallize a 4-chloro-2-fluoro-substituted-phenylboronic acid, like PBA, or a 4-chloro-2-fluoro-3-substituted-phenylboronic acid ester, like PBE. For example, a 4-chloro-2-fluoro-3-substituted-phenylboronic acid ester crystalline solid may be more convenient to store and transport than a 4-chloro-2-fluoro-3-substituted-phenylboronic acid ester solution. Disadvantageously, PBE has a relatively low melting point, which may impair or preclude an efficient crystallization thereof. The PBE melting point is 39-41° C. A need thus remains for a 4-chloro-2-fluoro-3-substituted-phenylboronic acid ester that has a relatively higher melting point and that can be efficiently formed and efficiently used in subsequent processes, such as the production of herbicide intermediates.

BRIEF SUMMARY

An embodiment of the present disclosure includes a method of forming a 4-chloro-2-fluoro-3-substituted-phenylboronic acid pinacol ester that comprises contacting a 1-chloro-3-fluoro-2-substituted benzene with an alkyl lithium to form a lithiated 1-chloro-3-fluoro-2-substituted benzene. The lithiated 1-chloro-3-fluoro-2-substituted benzene may be contacted with an electrophilic boronic acid derivative to form a 4-chloro-2-fluoro-3-substituted-phenylboronate. The 4-chloro-2-fluoro-3-substituted-phenylboronate may be reacted with an aqueous base to form a (4-chloro-2-fluoro-3-substituted-phenyl)trihydroxyborate. The (4-chloro-2-fluoro-3-substituted-phenyl)trihydroxyborate may be reacted with an acid to form a 4 chloro-2-fluoro-3-substituted-phenylboronic acid. The 4-chloro-2-fluoro-3-substituted-phenylboronic acid may be reacted with 2,3-dimethyl-2,3-butanediol.

Another embodiment of the present disclosure includes a method of forming 2-(4-chloro-2-fluro-3-methoxylphenyl)-4,4,5,5-tetramethyl-1,3,2-dioxaborolane that comprises contacting 2-chloro-6-fluoroanisole with n-butyl lithium to form 6-chloro-2-fluoro-3-lithioanisole. The 6-chloro-2-fluoro-3-lithioanisole may be contacted with trimethyl borate to form dimethyl 4-chloro-2-fluoro-3-methoxyphenylboronate. The dimethyl 4-chloro-2-fluoro-3-methoxyphenylboronate may be reacted with aqueous potassium hydroxide to form potassium (4-chloro-2-fluoro-3-methoxyphenyl)trihydroxyborate. The potassium (4-chloro-2-fluoro-3-methoxyphenyl)trihydroxyborate then may be reacted with aqueous hydrochloric acid to form 4-chloro-2-fluoro-3-methoxyphenylboronic acid. The 4-chloro-2-fluoro-3-methoxyphenylboronic acid may be reacted with 2,3-dimethyl-2,3-butanediol.

Yet another embodiment of the present disclosure includes a method of using a 4-chloro-2-fluoro-3-substituted-phenylboronic acid pinacol ester comprising reacting the 4-chloro-2-fluoro-3-substituted-phenylboronic acid pinacol ester with methyl 4-acetamido-3,6-dichloropicolinate to produce a 6-(4-chloro-2-fluoro-3-substituted-phenyl)-4-aminopicolinate.

Yet still another embodiment of the present disclosure includes a 4-chloro-2-fluoro-3-substituted-phenylboronic acid pinacol ester produced by introducing 2,3-dimethyl-2,3-butanediol into a solution comprising a 4-chloro-2-fluoro-3-substituted-phenylboronic acid, wherein the 4-chloro-2-fluoro-3-substituted-phenylboronic acid pinacol ester is obtained at a yield of greater than approximately 90%.

DETAILED DESCRIPTION

Methods of forming 4-chloro-2-fluoro-3-substituted-phenylboronic acid pinacol esters, such as PBE-pinacol are disclosed, as well as methods of using the 4-chloro-2-fluoro-3-substituted-phenylboronic acid pinacol esters. A 1-chloro-3-fluoro-2-substituted benzene may be reacted with an alkyl lithium and an electrophilic boronic acid derivative to form a 4-chloro-2-fluoro-3-substituted-phenylboronate. The 4-chloro-2-fluoro-3-substituted-phenylboronate may be converted to a 4-chloro-2-fluoro-3-substituted-phenylboronic acid by treatment with an aqueous base followed by acidification. The 4-chloro-2-fluoro-3-substituted-phenylboronic acid may be condensed with 2,3-dimethyl-2,3-butanediol (pinacol) to form the 4-chloro-2-fluoro-3-substituted-phenylboronic acid pinacol ester. The 4-chloro-2-fluoro-3-substituted-phenylboronic acid pinacol ester may be used in further reactions, such as a Suzuki coupling reaction, to produce additional chemical compounds, such as 6-(4-chloro-2-fluoro-3-substituted-phenyl)-4-aminopicolinates.

A reaction scheme for the preparation of a 4-chloro-2-fluoro-3-substituted-phenylboronic acid pinacol ester from a 1-chloro-3-fluoro-2-substituted benzene is shown below:

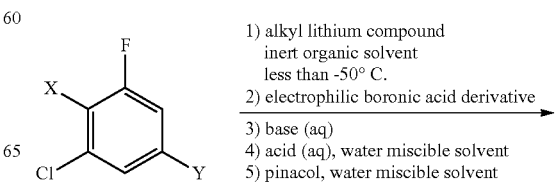

-continued

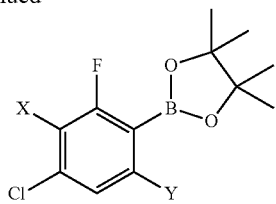

where X is F, OR₁, or NR₂R₃, Y is H or F, each of $R_1$, $R_2$, and $R_3$ is independently a methyl group, an ethyl group, a propyl group, or a butyl group. The reaction scheme is described in detail below.

An alkyl lithium may be added or introduced to the 1-chloro-3-fluoro-2-substituted benzene to facilitate a lithiation reaction between the 1-chloro-3-fluoro-2-substituted benzene and the alkyl lithium and form a reaction mixture including a lithiated 1-chloro-3-fluoro-2-substituted benzene. In at least some embodiments, the 1-chloro-3-fluoro-2-substituted benzene is 2-chloro-6-fluoroanisole (2,6-CFA). 1-chloro-3-fluoro-2-substituted benzenes may be produced by conventional techniques, which are not described in detail herein. The alkyl lithium may be any compound that includes a lithium and an alkyl functional group (i.e., of straight chain, branched chain, or cyclic configuration), such as methyl, ethyl, 1-methylethyl, propyl, cyclopropyl, butyl, 1,1-dimethylethyl, cyclobutyl, 1-methylpropyl, or hexyl. By means of non-limiting example, the alkyl lithium may include methyl lithium, n-butyl lithium (n-BuLi), s-butyl lithium, t-butyl lithium, or propyl lithium. In one or more embodiments, the alkyl lithium is n-BuLi. Alkyl lithiums are commercially available from numerous sources, including but not limited to, Sigma-Aldrich Co. (St. Louis, MO). In embodiments where the 1-chloro-3-fluoro-2-substituted benzene is 2,6-CFA and the alkyl lithium is n-BuLi, the lithiated 1-chloro-3-fluoro-2-substituted benzene may be 6-chloro-2-fluoro-3-lithioanisole (Li-2,6-CFA).

The lithiation reaction may be conducted in an inert organic solvent in which the 1-chloro-3-fluoro-2-substituted benzene is at least partially soluble. In one or more embodiments, the 1-chloro-3-fluoro-2-substituted benzene is at least substantially dissolved in the inert organic solvent. The inert organic solvent may include, but is not limited to, a $C_5$-$C_8$ hydrocarbon (i.e., of straight-chain, branched, or cyclic configuration), such as a pentane, a hexane, a cyclohexane, an iso-octane, an ether (e.g., diethyl ether, tetrahydrofuran, dioxane, glycol ethers including 1,2-dimethoxyethane), or combinations thereof. In at least some embodiments, the inert organic solvent is 1,2-dimethoxyethane (DME).

At least one molar equivalent of the alkyl lithium may be used relative to the 1-chloro-3-fluoro-2-substituted benzene. The alkyl lithium may be added in a slight excess relative to the 1-chloro-3-fluoro-2-substituted benzene compound, such as from about 1% to about 10% molar excess relative to the 1-chloro-3-fluoro-2-substituted benzene, or from about 2% to about 5% molar excess relative to the 1-chloro-3-fluoro-2-substituted benzene. The lithiation reaction may be conducted under anhydrous conditions, at atmospheric pressure or greater, and at a temperature of less than or equal to about −30° C., preferably less than −50° C., such as less than about −65° C. The reaction mixture may be agitated (e.g., via stirring, ultrasonically agitating, shaking a containment vessel) for a sufficient amount of time to facilitate the deprotonation of the 1-chloro-3-fluoro-2-substituted benzene at a position (C4) between a carbon atom (C3) to which the fluoro substituent is bonded and another carbon atom (C5) to which the Y group is bonded. The lithiation reaction may be conducted under an inert atmosphere, such as under a nitrogen ($N_2$) atmosphere.

An electrophilic boronic acid derivative may be added or introduced to the reaction mixture to react with or contact the lithiated 1-chloro-3-fluoro-2-substituted benzene and form a phenyl boronate solution including a 4-chloro-2-fluoro-3-substituted-phenylboronate. The electrophilic boronic acid derivative may be a trialkyl borate, such as trimethyl borate ($B(OMe)_3$), triethyl borate ($B(OEt)_3$), or triisopropyl borate ($B(Oi-Pr)_3$). In at least some embodiments, the electrophilic boronic acid derivative is $B(OMe)_3$. In embodiments in which the electrophilic boronic acid derivative is $B(OMe)_3$ and the lithiated 1-chloro-3-fluoro-2-substituted benzene is Li-2,6-CFA, the 4-chloro-2-fluoro-3-substituted-phenylboronate may be dimethyl 4-chloro-2-fluoro-3-methoxyphenylboronate (PBA-diMe). The electrophilic boronic acid derivative may be added slowly, while maintaining a temperature of the reaction mixture of less than or equal to −30° C., preferably less than −50° C., such as less than about −65° C. The reaction mixture may be agitated for an amount of time sufficient for the electrophilic boronic acid derivative to react with lithiated 1-chloro-3-fluoro-2-substituted benzene. By the end of the reaction the salinated phenyl boronate solution may have a temperature within a range of from about 20° C. to about 25° C. (e.g., ambient temperature).

An aqueous base may be added or introduced to the phenyl boronate solution to react with or hydrolyze the 4-chloro-2-fluoro-3-substituted-phenylboronate and form a first multi-phase solution including a (4-chloro-2-fluoro-3-substituted-phenyl)trihydroxyborate. The aqueous base may include a base of sufficient strength to hydrolyze the 4-chloro-2-fluoro-3-substituted-phenylboronate. By means of non-limiting example, the aqueous base may include potassium hydroxide (KOH), sodium hydroxide (NaOH), or combinations thereof. In at least some embodiments, the aqueous base is aqueous KOH. In embodiments where the 4-chloro-2-fluoro-3-substituted-phenylboronate is PBA-diMe and the aqueous base is KOH, the (4-chloro-2-fluoro-3-substituted-phenyl)trihydroxyborate may be potassium (4-chloro-2-fluoro-3-methoxyphenyl) trihydroxyborate (PBA-K). Adding or introducing the aqueous base to the phenyl boronate solution may yield a first multi-phase solution having a greater temperature than the phenyl boronate solution. Optionally, a cooling means (e.g., a water bath for the reaction vessel) may be provided to control a temperature of the first multi-phase solution, such that the temperature remains within a range of from about 25° C. to about 30° C. The first multi-phase solution may be agitated for a sufficient amount of time for the aqueous base to hydrolyze the 4-chloro-2-fluoro-3-substituted-phenylboronate. The first multi-phase solution may then be separated into a first organic phase and a first aqueous phase (e.g., by transferring the first multi-phase solution into a separation vessel, such as a separatory funnel). The first organic phase may be discarded, while the first aqueous phase, which includes the (4-chloro-2-fluoro-3-substituted-phenyl)trihydroxyborate, may be further treated, as described in detail below.

At least one acid may be added or introduced to the first aqueous phase to react with or protonate the (4-chloro-2-fluoro-3-substituted-phenyl)trihydroxyborate and form a phenyl boronic acid solution including a 4-chloro-2-fluoro-3-substituted-phenylboronic acid. By means of non-limiting example, the at least one acid may include hydrochloric acid (HCl). Other acids include hydrobromic acid (HBr), sulfuric acid ($H_2SO_4$), methane sulfonic acid and para-toluene sulfonic acid. The at least one acid may be used neat or may be diluted with a solvent. In at least some embodiments, the acid is 6M aqueous HCl. An equimolar amount or an excess amount of the at least one acid relative to the (4-chloro-2-fluoro-3-substituted-phenyl)trihydroxyborate may be used. In embodiments where the (4-chloro-2-fluoro-3-substituted-phenyl)trihydroxyborate is PBA-K, the 4-chloro-2-fluoro-3-substituted-phenylboronic acid formed may be 4-chloro-2-fluoro-3-methoxyphenylboronic acid (PBA). Optionally, a cooling means may be provided to control the temperature of the phenyl boronic acid solution such that the temperature remains within a range of from about 25° C. to about 30° C. The phenyl boronic acid solution may be agitated for a sufficient amount of time to enable a substantial conversion of the (4-chloro-2-fluoro-3-substituted-phenyl)trihydroxyborate to the 4-chloro-2-fluoro-3-substituted-phenylboronic acid.

A water miscible solvent may be added or introduced to the phenyl boronic acid solution to form a second multi-phase solution. The 4-chloro-2-fluoro-3-substituted-phenylboronic acid may be substantially soluble in the water miscible organic solvent relative to its solubility in the phenyl boronic acid solution such that the second multi-phase solution may have a second organic phase that includes the 4-chloro-2-fluoro-3-substituted-phenylboronic acid and the water miscible solvent. The second organic phase may also include the inert organic solvent and water. The water miscible organic solvent may be compatible with subsequent reactions involving the 4-chloro-2-fluoro-3-substituted-phenylboronic acid such that a solvent exchange need not be conducted. By means of non-limiting example, the water miscible solvent may be 4-methyl-2-pentanone (i.e., methyl isobutyl ketone)(MIBK), acetonitrile (MeCN), ethyl acetate (EtOAc), or combinations thereof. In a particular embodiment, toluene can also be used. In at least some embodiments, the water miscible solvent is MIBK. Optionally, a salt, such as potassium chloride (KCl), sodium chloride (NaCl), calcium chloride ($CaCl_2$), sodium bromide (NaBr), potassium bromide (KBr), sodium sulfate ($Na_2SO_4$), ammonium chloride ($NH_4Cl$), or combinations thereof, may be added or introduced to at least one of the aqueous phase of the first multi-phase solution, the phenyl boronic acid solution, and the second multi-phase solution to minimize the amount of water in the second organic phase. The second organic phase may then be separated from a second aqueous phase of the second multi-phase solution (e.g., via a separatory funnel). Optionally, the second organic phase may be desolvated under reduced pressure or by crystallization to isolate the 4-chloro-2-fluoro-3-substituted-phenylboronic acid as a solid.

Pinacol may be added or introduced to the second organic phase or to a solution including the 4-chloro-2-fluoro-3-substituted-phenylboronic acid (e.g., a 4-chloro-2-fluoro-3-substituted-phenylboronic acid isolated as a solid and then dissolved in a solvent such as MIBK, MeCN, EtOAc, or combinations thereof) to facilitate a condensation reaction between the pinacol and the 4-chloro-2-fluoro-3-substituted-phenylboronic acid and form a pinacol ester solution including a 4-chloro-2-fluoro-3-substituted-phenylboronic acid pinacol ester. The pinacol may be used neat or in a water miscible solvent, such as MIBK, MeCN, EtOAc, or combinations thereof. In at least some embodiments, the pinacol is solvated with MIBK. In embodiments where the 4-chloro-2-fluoro-3-substituted-phenylboronic acid is PBA, the condensation reaction may form PBE-pinacol. The 4-chloro-2-fluoro-3-substituted-phenylboronic acid pinacol ester may remain in solution and may be used directly in subsequent reactions without additional concentration or drying. Optionally, the pinacol ester solution may be desolvated under reduced pressure or by crystallization to isolate the 4-chloro-2-fluoro-3-substituted-phenylboronic acid pinacol ester as a crystalline solid.

The detailed reaction scheme below illustrates a representative conversion of 2,6-CFA to PBE-pinacol:

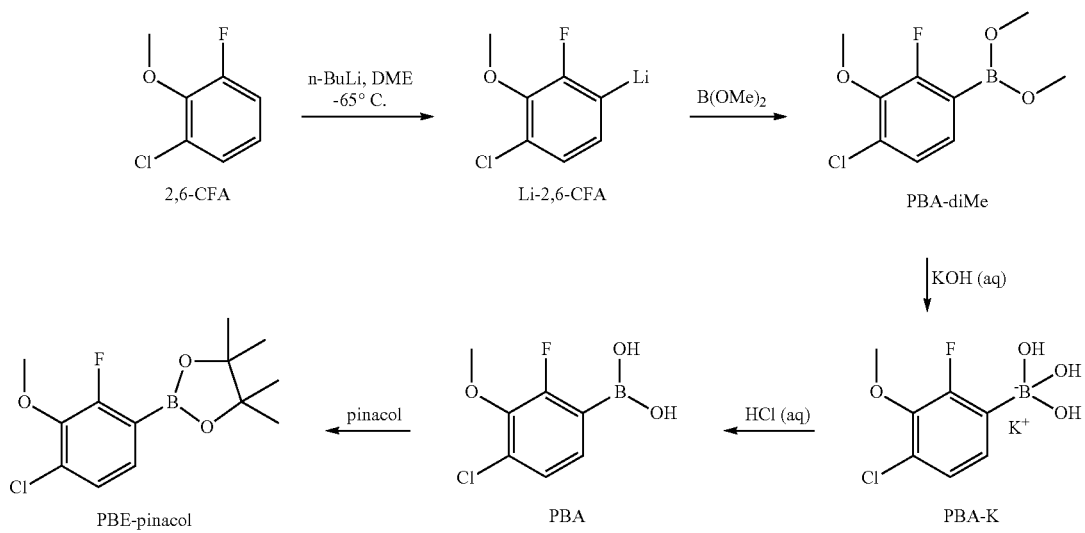

2,6-CFA may be reacted with n-BuLi in anhydrous DME at a temperature less than or equal to −30° C., preferably less than −50° C., such as less than about −65° C. to form the reaction mixture including Li-2,6-CFA. $B(OMe)_3$ may be added or introduced to the reaction mixture, where it may contact the Li-2,6,CFA and form the phenyl boronate solution including PBA-diMe. KOH in water may be added or introduced to the phenyl boronate solution at ambient temperature to react with the PBA-diMe and form the first multi-phase solution including PBA-K. After agitation, the first aqueous and the first organic phase of the first multi-phase solution may be separated. The first aqueous phase, which includes the PBA-K, may be acidified with 6 M aqueous HCl and agitated to form the phenyl boronic acid solution including PBA. MIBK may be added or introduced to the phenyl boronic acid solution to form the second multi-phase solution having the second organic phase including PBA, DME, and MIBK. The second organic phase may be separated and reacted with pinacol in MIBK to form the pinacol ester solution including PBE-pinacol. A yield of the PBE-pinacol may be greater than or equal to about 90%, such as greater than or equal to about 95%.

The pinacol ester solution or a 4-chloro-2-fluoro-3-substituted-phenylboronic acid pinacol ester crystalline solid, may be utilized in additional chemical reactions, such as a Suzuki coupling reaction. By means of non-limiting example, the pinacol ester solution (or the 4-chloro-2-fluoro-3-substituted-phenylboronic acid pinacol ester crystalline solid) may undergo a cross-coupling reaction with methyl 4-acetamido-3,6-dichloropicolinate (i.e., acetylated aminopyralid methyl ester)(AcAP-Me) to produce or form a 6-(4-chloro-2-fluoro-3-substituted-phenyl)-4-aminopicolinate, such as methyl 4-acetamido-3-chloro-6-(4-chloro-2-fluoro-3-methoxyphenyl)picolinate (Ac729-Me). PBE-pinacol may be used to produce 2-(4-chloro-2-fluoro-3-methoxyphenyl)-6-amino-4-pyrimidinecarboxylic acid. The coupling partner to PBE-pinacol may be methyl 6-acetamido-2-chloropyrimidine-4-carboxylate or its unprotected version the 6-amino-2-chloropyrimidine-4-carboxylic acid. The cross-coupling reaction may occur in the presence of a palladium catalyst, a ligand, and a base. In at least some embodiments, the palladium catalyst is palladium(II)acetate ($Pd(OAc)_2$), the base is aqueous potassium carbonate ($K_2CO_3$), and the ligand is triphenylphosphine ($PPh_3$). The AcAP-Me may be used neat or may be provided in a solvent such as MIBK, MeCN, EtOAc, water, or combinations thereof.

The palladium catalyst, the ligand, and the base may be added to a deoxygenated mixture including the AcAP-Me and the pinacol ester solution (or the 4-chloro-2-fluoro-3-substituted-phenylboronic acid pinacol ester crystalline solid) to form a coupling reaction mixture. The coupling reaction mixture may be agitated at a temperature within a range of from about 40° C. to about 70° C. for a sufficient amount to time to complete a cross-coupling reaction and form a third multi-phase solution having an third organic phase including the 6-(4-chloro-2-fluoro-3-substituted-phenyl)-4-aminopicolinate. The palladium catalyst may be removed (e.g., by exposing the third multi-phase solution to celite), and the third organic phase may be separated or extracted. In embodiments where the coupling reaction mixture includes PBE-pinacol and AcAP-Me, a yield of Ac729-Me may be greater than about 85%, such as greater than about 87%, or greater than about 90%.

4-chloro-2-fluoro-3-substituted-phenylboronic acid pinacol esters may be formed at generally high yields (e.g., greater than or equal to 90% yield of PBE-pinacol), and may be used as intermediates to obtain generally high yields of desired products (e.g., greater than or equal to 85% yield of Ac729-Me). 4-chloro-2-fluoro-3-substituted-phenylboronic acid pinacol esters may also have relatively higher melting points (e.g., from about 61° C. to about 62° C. for PBE-pinacol), enabling the efficient isolation of 4-chloro-2-fluoro-3-substituted-phenylboronic acid pinacol esters as crystalline solids. Being able to isolate 4-chloro-2-fluoro-3-substituted-phenylboronic acid pinacol esters as crystalline solids enables the use of 4-chloro-2-fluoro-3-substituted-phenylboronic acid pinacol esters in operations where at least one of the storage, transportation, and use of a 4-chloro-2-fluoro-3-substituted-phenylboronic acid ester solution would be inconvenient or unfavorable.

The following examples serve to explain embodiments of the present disclosure in more detail. These examples are not to be construed as being exhaustive or exclusive as to the scope of this invention.

EXAMPLES

Example 1

Synthesis and Isolation of PBA 2,6-CFA (10.0 g, 62. 28 mmol) was weighed in a separate flask and transferred to a 3-neck, 500-ml round bottom flask equipped with a thermocouple temperature probe, stir bar, and a $N_2$ inlet. The flask was rinsed with anhydrous DME. Additional DME was added to the reaction flask to give a total DME volume of 106 ml. The reaction was cooled to −78° C. with a dry ice/acetone bath. Once the reaction reached −77° C., n-BuLi (29 ml, 71.62 mmol, 2.5 M in hexanes) was added slowly, dropwise, using a syringe pump over a 45 minute period. The highest temperature reached during addition was −70.1° C. After complete addition of n-BuLi, the reaction was left to stir for 1 hour at −74.1° C. After 1 hour, $B(OMe)_3$ (10.5 ml, 93.42 mmol) was added dropwise using a syringe pump over a period of 22 minutes. The highest temperature reached during the $B(OMe)_3$ addition was −67.0° C. After the complete addition of $B(OMe)_3$, the dry ice/acetone bath was removed and the reaction mixture warmed to room temperature (about 23.1° C.). Once the reaction mixture reached room temperature, the reaction was left to stir an additional 1 hour at that temperature. This procedure was repeated several times to generate a large amount of PBA-diMe in DME. 244.0 g of PBA-diMe in DME (10.3% PBA basis), 27.82 g of 45% KOH, and 108.70 g of deionized water were added to a one liter flask containing a magnetic stirrer. The one liter flask was cooled with a cold water bath to maintain a temperature of 25° C. to 30° C. during the additions. The mixture was stirred for about 2 h and was then vacuum filtered to remove lithium salts. Aqueous and organic phases of the mixture were then separated. Concentrated HCl (40.48 g) was added to the aqueous phase. The aqueous phase was cooled with a cold water bath during the addition of the HCl to maintain a temperature of 25° C. to 30° C. The aqueous phase was stirred for about 15 minutes to achieve complete dissolution. MIBK (35.91 g) was added to the aqueous phase and the aqueous phase was stirred for about 15 minutes. An organic phase separated from an aqueous phase to give 127.6 g of the organic phase. Analysis of the organic phase gave 17.57% by weight (89.1% yield) of PBA. The organic phase was concentrated to dryness and then placed in a vacuum oven at 50° C. to give a white solid.

Example 2

Formation of PBE-pinacol from PBA

PBA solid (3.0 g, 14.68 mmol) was added to a 100 mL round bottom flask equipped with a magnetic stirrer and $N_2$ inlet. The PBA solid was dissolved in EtOAc (35 mL) and pinacol (1.7 g, 14.7 mmol) was added. The mixture was stirred for 2 hours at room temperature (approximately 23.1° C.). After 2 hours the reaction was complete. The reaction mixture was concentrated under reduced pressure to give an oil that, when placed on high vacuum, gave a crystalline solid of PBE-pinacol in >99% yield. A portion of the crystalline solid was purified using column chromatography using a 8:1 Hexane/EtOAc ratio (v/v) to give a PBE-pinacol solid that had a melting point of 61° C. to 62° C.

Example 3

Use of PBE-pinacol to Produce an Herbicide Intermediate

PBE-pinacol (2.61 g, 9.12 mmol), acetylated aminopyralid methyl ester (2.0 g, 7.6 mmol), triphenyl phosphine (20 mg, 0.076 mmol), and palladium(II) acetate (9 mg, 0.038 mmol) were added, under a $N_2$ atmosphere, to a 50 mL 3-neck round bottom flask equipped with a condenser, thermocouple temperature probe, magnetic stir bar, and $N_2$ inlet. The solvents, MIBK (10 mL) and MeCN (3.0 mL), were sparged separately with $N_2$ for 30 minutes with stirring then added to the reaction flask. The reaction mixture was stirred for 5 minutes before adding an aqueous solution of $K_2CO_3$ (22.8%, 11.4 mL, 22.8 mmol, previously sparged for 30 minutes with $N_2$). The reaction mixture was heated to 60° C. and stirred for 2 hours. After 2 hours, the reaction was sampled by GC to determine completion of the reaction. Once the reaction was complete, the mixture was transferred to a heated separatory funnel and the phases separated. The organic phase was sample by GC with an internal standard (valerophenone) to yield 87% (2.53 g) Ac729-Me.

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of forming and using a 4-chloro-2-fluoro-3-substituted-phenylboronic acid pinacol ester, comprising:
    contacting a 1-chloro-3-fluoro-2-substituted benzene with an alkyl lithium to form a lithiated 1-chloro-3-fluoro-2-substituted benzene;
    contacting the lithiated 1-chloro-3-fluoro-2-substituted benzene with an electrophilic boronic acid derivative to form a 4-chloro-2-fluoro-3-substituted-phenylboronate;
    reacting the 4-chloro-2-fluoro-3-substituted-phenylboronate with an aqueous base to form a (4-chloro-2-fluoro-3-substituted-phenyl)trihydroxyborate;
    reacting the (4-chloro-2-fluoro-3-substituted-phenyl)trihydroxyborate with an acid to form a 4-chloro-2-fluoro-3-substituted-phenylboronic acid;
    reacting the 4-chloro-2-fluoro-3-substituted-phenylboronic acid with 2,3-dimethyl-2,3-butanediol to form a 4-chloro-2-fluoro-3-substituted-phenylboronic acid pinacol ester; and
    subjecting the 4-chloro-2-fluoro-3-substituted-phenylboronic acid pinacol ester to a Suzuki's coupling reaction in a medium consisting of a Suzuki's coupling reactant, a palladium catalyst, a ligand, at least one solvent, and a base,
    wherein the Suzuki's coupling reactant is a methyl 4-acetamido-3,6-dichloropicolinate to produce a 6-(4-chloro-2-fluoro-3-substituted-phenyl)-4-aminopicolinate, or
    wherein the Suzuki's coupling reactant is a methyl 6-acetamido-2-chloropyrimidine-4-carboxylate or a 6-amino-2-chloropyrimidine-4-carboxylic acid to produce a 6-(4-chloro-2-fluoro-3-substituted-phenyl)-4-aminopicolinate.

2. The method of claim 1, wherein reacting the 4-chloro-2-fluoro-3-substituted-phenylboronic acid with 2,3-dimethyl-2,3-butanediol comprises obtaining a yield of the 4-chloro-2-fluoro-3-substituted-phenylboronic acid pinacol ester of greater than or equal to about 90%.

3. The method of claim 1, wherein contacting the 1-chloro-3-fluoro-2-substituted benzene with the alkyl lithium comprises introducing an alkyl lithium into a solution comprising the 1-chloro-3-fluoro-2-substituted benzene and an anhydrous solvent to form a reaction mixture comprising the lithiated 1-chloro-3-fluoro-2-substituted benzene.

4. The method of claim 3, wherein contacting the lithiated 1-chloro-3-fluoro-2-substituted benzene with the electrophilic boronic acid derivative comprises adding the electrophilic boronic acid derivative to the reaction mixture to form a phenyl boronate solution comprising the 4-chloro-2-fluoro-3-substituted-phenylboronate.

5. The method of claim 4, wherein reacting the 4-chloro-2-fluoro-3-substituted-phenylboronate with the aqueous base comprises adding the aqueous base to the phenyl boronate solution to form a first multi-phase solution comprising a first aqueous phase and a first organic phase, the first aqueous phase comprising the (4-chloro-2-fluoro-3-substituted-phenyl)trihydroxyborate.

6. The method of claim 5, wherein reacting the (4-chloro-2-fluoro-3-substituted-phenyl)trihydroxyborate with an acid comprises:
    separating the first aqueous phase and the first organic phase; and
    adding the acid to the first aqueous phase to form a phenyl boronic acid solution comprising the 4-chloro-2-fluoro-3-substituted-phenylboronic acid.

7. The method of claim 6, wherein reacting the 4-chloro-2-fluoro-3-substituted-phenylboronic acid with the 2,3-dimethyl-2,3-butanediol comprises:
    adding a water miscible solvent to the phenyl boronic acid solution to form a second multi-phase solution comprising a second aqueous phase and a second organic phase, the second organic phase comprising the 4-chloro-2-fluoro-3-substituted-phenylboronic acid;
    separating the second aqueous phase and the second organic phase; and
    introducing the 2,3-dimethyl-2,3-butanediol into the second organic phase to form a pinacol ester solution comprising the 4-chloro-2-fluoro-3-substituted-phenylboronic acid pinacol ester.

8. The method of claim 7, wherein adding a water miscible solvent solution to the phenyl boronic acid solution comprises adding at least one of 4-methyl-2-pentanone, acetonitrile, and ethyl acetate to the phenyl boronic acid solution.

9. A method of forming and using 2-(4-chloro-2-fluoro-3-methoxyphenyl)-4,4,5,5-tetramethy- 1,3,2-dioxaborolane, comprising:
    contacting 2-chloro-6-fluoroanisole with n-butyl lithium to form 6-chloro-2-fluoro-3-lithioanisole;
    contacting the 6-chloro-2-fluoro-3-lithioanisole with trimethyl borate to form dimethyl 4-chloro-2-fluoro-3-methoxyphenylboronate;

reacting the dimethyl 4-chloro-2-fluoro-3-methoxyphenylboronate with aqueous potassium hydroxide to form potassium (4-chloro-2-fluoro-3-methoxyphenyl)trihydroxyborate;

reacting the potassium (4-chloro-2-fluoro-3-methoxyphenyl)trihydroxyborate with aqueous hydrochloric acid to form 4-chloro-2-fluoro-3-methoxyphenylboronic acid;

reacting the 4-chloro-2-fluoro-3-methoxyphenylboronic acid with 2,3-dimethyl-2,3-butanediol to form a 2-(4-chloro-2-fluoro-3-methoxyphenyl)-4,4,5,5-tetramethyl-1,3,2-dioxaborolane; and subjecting the 2-(4-chloro-2-fluoro-3-methoxyphenyl)-4,4,5,5-tetramethyl-1,3,2-dioxaborolane to a Suzuki's coupling reaction in a medium consisting of a Suzuki's coupling reactant, a palladium catalyst, a ligand, at least one solvent, and a base, wherein the Suzuki's coupling reactant comprises at least one of methyl 4-acetamido-3,6-dichloropicolinate, methyl 6-acetamido-2-chloropyrimidine-4-carboxylate, or 6-amino-2-chloropyrimidine-4-carboxylic acid.

10. The method of claim 9, wherein reacting the 4-chloro-2-fluoro-3-methoxyphenylboronic acid with the 2,3-dimethyl-2,3-butanediol comprises obtaining a yield of the 2-(4-chloro-2-fluoro-3-methoxylphenyl)-4,4,5,5-tetramethyl-1,3,2-dioxaborolane of greater than or equal to about 90%.

11. The method of claim 9, wherein contacting the 2-chloro-6-fluoroanisole with the n-butyl lithium comprises introducing n-butyl lithium into a solution comprising the 2-chloro-6-fluoroanisole and at least one of 1,2-dimethoxyethane, diethyl ether, tetrahydrofuran, and dioxane to form a reaction mixture comprising the 6-chloro-2-fluoro-3-lithioanisole.

12. The method of claim 11, wherein contacting the 6-chloro-2-fluoro-3-lithioanisole with the trimethyl borate comprises adding the trimethyl borate to the reaction mixture to form a phenyl boronate solution comprising the dimethyl 4-chloro-2-fluoro-3-methoxyphenylboronate.

13. The method of claim 12, wherein reacting the dimethyl 4-chloro-2-fluoro-3-methoxyphenylborate with the aqueous potassium hydroxide comprises adding the aqueous potassium hydroxide to the phenyl boronate solution to form a first multi-phase solution comprising a first aqueous phase and a first organic phase, the first aqueous phase comprising the potassium (4-chloro-2-fluoro-3-methoxyphenyl)trihydroxyborate.

14. The method of claim 13, wherein reacting the potassium (4-chloro-2-fluoro-3-methoxyphenyl)trihydroxyborate with the aqueous hydrochloric acid comprises:

separating the first aqueous phase and the first organic phase; and adding the aqueous hydrochloric acid to the first aqueous phase to form a phenyl boronic acid solution comprising the 4-chloro-2-fluoro-3-methoxyphenylboronic acid.

15. The method of claim 14, wherein reacting the 4-chloro-2-fluoro-3-methoxyphenylboronic acid with the 2,3-dimethyl-2,3-butanediol comprises:

adding at least one of 4-methyl-2-pentanone, acetonitrile, and ethyl acetate to the phenyl boronic acid solution to form a second multi-phase solution comprising a second aqueous phase and a second organic phase, the second organic phase comprising the 4-chloro-2-fluoro-3-methoxyphenylboronic acid;

separating the second aqueous phase and the second organic phase; and introducing the 2,3-dimethyl-2,3-butanediol into the second organic phase to form a pinacol ester solution comprising the 2-(4-chloro-2-fluoro-3-methoxylphenyl)-4,4,5,5-tetramethyl-1,3,2-dioxaborolane.

* * * * *